US00PP25978P2

(12) United States Plant Patent
Blom

(10) Patent No.: US PP25,978 P2
(45) Date of Patent: Oct. 6, 2015

(54) *HELENIUM* PLANT NAMED 'SALSA'

(50) Latin Name: *Helenium hybrida*
Varietal Denomination: Salsa

(71) Applicant: Arie Blom, Oudewater (NL)

(72) Inventor: Arie Blom, Oudewater (NL)

(73) Assignee: AB Kwekersrechten B.V., Zuidwolde (NL)

( * ) Notice: Subject to any disclaimer, the term of this patent is extended or adjusted under 35 U.S.C. 154(b) by 108 days.

(21) Appl. No.: 13/998,998

(22) Filed: Dec. 31, 2013

(51) Int. Cl.
*A01H 5/00* (2006.01)

(52) U.S. Cl.
USPC ..... Plt./435

(58) Field of Classification Search
USPC ..... Plt./435
See application file for complete search history.

(56) References Cited

PUBLICATIONS

PLUTO Plant Variety database Jun. 9, 2015. p. 1.*

* cited by examiner

*Primary Examiner* — Annette Para
(74) *Attorney, Agent, or Firm* — C A. Whealy

(57) ABSTRACT

A new and distinct cultivar of *Helenium* plant named 'Salsa', characterized by its compact and upright plant habit; moderately vigorous to vigorous growth habit; freely flowering habit; inflorescences with dark red-colored ray florets with yellow-colored bases giving a "halo" effect around the disc; and strong peduncles that hold the inflorescences above the foliar plane.

3 Drawing Sheets

Botanical designation: *Helenium hybrida.*
Cultivar denomination: 'SALSA'.

BACKGROUND OF THE INVENTION

The present invention relates to a new and distinct cultivar of *Helenium* plant, botanically known as *Helenium hybrida* and hereinafter referred to by the name 'Salsa'.

The new *Helenium* plant is a product of a planned breeding program conducted by the Inventor in Zuidwolde, The Netherlands. The objective of the program is to create and develop new compact *Helenium* plants with attractive ray and disc colors.

The new *Helenium* plant originated from an open-pollination in 2008 of *Helenium hybrida* 'Ruby Tuesday', disclosed in U.S. Plant Pat. No. 18,234, as the female, or seed, parent with an unknown selection of *Helenium hybrida* as the male, or pollen, parent. The new *Helenium* plant was discovered and selected by the Inventor as a single flowering plant within the progeny of the stated open-pollination in a controlled environment in Zuidwolde, The Netherlands in 2011.

Asexual reproduction of the new *Helenium* plant by terminal cuttings in a controlled greenhouse environment in Heerhugowaard, The Netherlands since 2011 has shown that the unique features of this new *Helenium* plant are stable and reproduced true to type in successive generations.

SUMMARY OF THE INVENTION

Plants of the new *Helenium* have not been observed under all possible combinations of environmental conditions and cultural practices. The phenotype may vary somewhat with variations in environmental conditions such as temperature, daylength and light intensity, without, however, any variance in genotype.

The following traits have been repeatedly observed and are determined to be the unique characteristics of 'Salsa'. These characteristics in combination distinguish 'Salsa' as a new and distinct *Helenium* plant:

1. Compact and upright plant habit.
2. Moderately vigorous to vigorous growth habit.
3. Freely flowering habit.
4. Inflorescences with dark red-colored ray florets with yellow-colored bases giving a "halo" effect around the disc.
5. Strong peduncles that hold the inflorescences above the foliar plane.

In side-by-side comparisons conducted in Zuidwolde, The Netherlands, plants of the new *Helenium* differed from plants of the female parent, 'Ruby Tuesday', primarily in ray floret color as plants of 'Ruby Tuesday' have solid dark red-colored ray florets. In addition, ray florets of plants of the new *Helenium* are flatter than ray florets of plants of 'Ruby Tuesday'.

Plants of the new *Helenium* can be compared to plants of *Helenium hybrida* 'Chelsey', disclosed in U.S. Plant Pat. No. 16,322. In side-by-side comparisons conducted in Zuidwolde, The Netherlands, plants of the new *Helenium* differed from plants of 'Chelsey' primarily in ray floret color as plants of 'Chelsey' had red-colored ray florets with yellow-colored streaks.

BRIEF DESCRIPTION OF THE PHOTOGRAPHS

The accompanying photographs illustrate the overall appearance of the new *Helenium* plant showing the colors as true as it is reasonably possible to obtain in colored reproductions of this type. Colors in the photographs may differ slightly from the color values cited in the detailed botanical description which accurately describe the colors of the new *Helenium* plant.

The photograph on the first sheet comprises a side perspective view of a typical flowering plant of 'Salsa'.

The photograph on the second sheet is a close-up view of typical inflorescences of 'Salsa'.

The photograph on the third sheet is a close-up view of typical leaves of 'Salsa'.

DETAILED BOTANICAL DESCRIPTION

The aforementioned photographs and following observations and measurements describe plants grown during the summer in ground beds in an outdoor nursery in Zuidwolde, The Netherlands and under cultural practices typical of commercial *Helenium* production. During the production of the plants, day temperatures ranged from 18° C. to 32° C. and night temperatures ranged from 8° C. to 20° C. Plants were one year old when the photographs and description were taken. In the following description, color references are made to The Royal Horticultural Society Colour Chart, 2007 Edition, except where general terms of ordinary dictionary significance are used.

Botanical classification: *Helenium hybrida* 'Salsa'.

Parentage:

*Female, or seed, parent.*—*Helenium hybrida* 'Ruby Tuesday', disclosed in U.S. Plant Pat. No. 18,234.

*Male, or pollen, parent.*—Unknown selection of *Helenium hybrida*, not patented.

Propagation:

*Type.*—Vegetative cuttings.

*Time to initiate roots, summer.*—About two weeks at temperatures about 20° C.

*Time to produce a rooted cutting, summer.*—About two months at temperatures about 20° C.

*Root description.*—Medium in thickness, fibrous; creamy white in color.

*Rooting habit.*—Moderately freely branching; medium density.

Plant description:

*Appearance and growth habit.*—Herbaceous perennial; compact and upright plant habit; inverted triangle; freely basal branching with about 18 flowering stems developing per plant; moderately vigorous to vigorous growth habit.

*Plant height.*—About 69 cm.

*Plant width or area of spread.*—About 59 cm.

*Lateral branch description.*—Appearance: Mostly rounded with three axial "wings"; wings about 2 mm in width. Length: About 29.3 cm. Diameter: About 3.5 mm. Internode length: About 2.8 cm. Strength: Strong. Aspect: About 20° from vertical. Texture: Smooth, glabrous. Color: Close to 144B; wings, close to 144A.

Leaf description:

*Arrangement.*—Alternate; simple; sessile.

*Length.*—About 8.1 cm.

*Width.*—About 2.3 cm.

*Shape.*—Narrowly elliptic to oblanceolate.

*Apex.*—Acute.

*Base.*—Cuneate; decurrent.

*Margin.*—Serrate.

*Venation pattern.*—Pinnate.

*Texture, upper and lower surfaces.*—Smooth, glabrous.

*Color.*—Developing leaves, upper surface: Close to 143A. Developing leaves, lower surface: Between 146B and 147B. Fully expanded leaves, upper surface: Close to N137A; venation, close to 144A. Fully expanded leaves, lower surface: Between 137B and 147B; venation, close to 144A.

Inflorescence description:

*Appearance and arrangement.*—Single terminal inflorescences held above the foliar plane on strong erect peduncles; composite inflorescence form, radially symmetrical; obcordate to flabellate-shaped ray florets; disc florets massed at the center; ray and disc florets develop acropetally on a capitulum; inflorescences face mostly upright.

*Natural flowering season.*—Plants flower continuous and freely from early August to early October in The Netherlands.

*Postproduction longevity.*—Inflorescences maintain good color and substance for about six weeks on the plant; inflorescences persistent.

*Quantity of inflorescences.*—Freely flowering habit; about 200 inflorescences developing per plant during the flowering season.

*Fragrance.*—None detected.

*Inflorescence buds.*—Length: About 8 mm. Diameter: About 1.8 cm. Shape: Flattened globular. Color: Close to 143B.

*Inflorescence size.*—Diameter: About 4.4 cm. Depth (height): About 1.6 cm. Disc diameter: About 1.7 cm. Receptacle height: About 6 mm. Receptacle diameter: About 7 mm.

*Ray florets.*—Quantity and arrangement: About 18 ray florets arranged in a single whorl. Length: About 2.1 cm. Width: About 1.4 cm. Shape: Obcordate to flabellate. Apex: Three to four-lobed; lobes, obtuse. Base: Cuneate. Margin: Entire. Texture, upper and lower surfaces: Smooth, glabrous; velvety; longitudinally ribbed. Orientation: Initially upright then perpendicular to the peduncle. Color: When opening, upper surface: Center and towards the apex, slightly darker than 185A; towards the base, tinged with close to 14B. When opening, lower surface: Center and towards the apex, slightly darker than 183A; towards the base, tinged with close to 14B. Fully opened opening, upper surface: Center and towards the apex, between N34A and 185A; towards the base, tinged with close to 14B; with development, main color becoming closer to between 175B and 183B. Fully opened, lower surface: Center and towards the apex, close to 183A to 183B; towards the base, tinged with close to 14B; with development, main color becoming closer to between 175B and 178A.

*Disc florets.*—Quantity and arrangement: Numerous, about 400 disc florets arranged spirally at the center of the receptacle. Length: About 4.5 mm. Width: About 1.2 mm. Shape: Tubular, elongated. Apex: Five-pointed; acute. Texture, inner and outer surfaces: Smooth, glabrous. Color, inner and outer surfaces, immature: Towards the apex, close to 200A; mid-section, close to 20A; towards the base, close to 145D. Color, inner and outer surfaces, mature: Towards the apex, close to 200B; mid-section, close to 20A; towards the base, close to 145D.

*Phyllaries.*—Quantity and arrangement: About 20 phyllaries arranged in a single whorl. Length: About 8 mm. Diameter: About 1.5 mm. Shape: Lanceolate. Apex: Narrowly acute. Base: Cuneate. Margin: Entire. Texture, upper and lower surfaces: Smooth, glabrous. Color, upper surface: Close to 143C. Color, lower surface: Close to 143B.

*Peduncles*.—Length, terminal peduncle: About 7.2 cm. Length, fourth peduncle: About 13.2 cm. Diameter: About 1.5 mm. Angle: Erect to about 25° from vertical. Strength: Strong. Texture: Smooth, glabrous. Color: Close to 144A.

*Reproductive organs*.—Androecium: Present on disc florets only. Stamen number: Four per floret. Filament length: About 1 mm. Filament color: Close to 161C. Anther shape: Lanceolate. Anther length: About 1 mm. Anther color: Close to N199A. Pollen amount: None observed. Gynoecium: Present on both ray and disc florets. Pistil number: One per floret. Pistil length: About 3 mm. Stigma shape: Decurrent. Stigma color: Close to 12A. Style length: About 2 mm. Style color: Close to 145D. Ovary color: Close to 145D.

*Fruits and seeds*.—Fruit and seed development have not been observed on plant of the new *Helenium*.

Disease & pest resistance: Resistance to pathogens and pests common to *Helenium* plants has not been observed on plants grown under outdoor conditions.

Garden performance: Plants of the new *Helenium* have been observed to have good garden performance and to tolerate rain, wind, high temperatures about 35° C. and to be hardy to USDA Hardiness Zone 5.

It is claimed:

1. A new and distinct *Helenium* plant named 'Salsa' as illustrated and described.

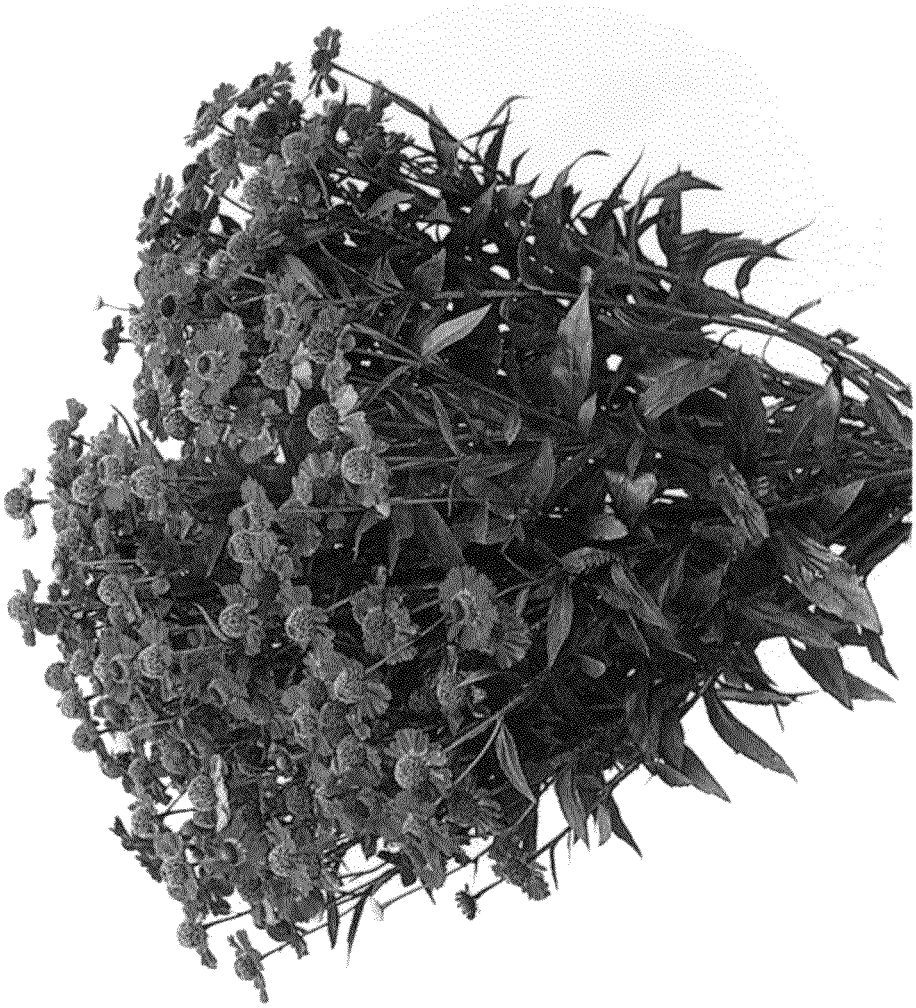

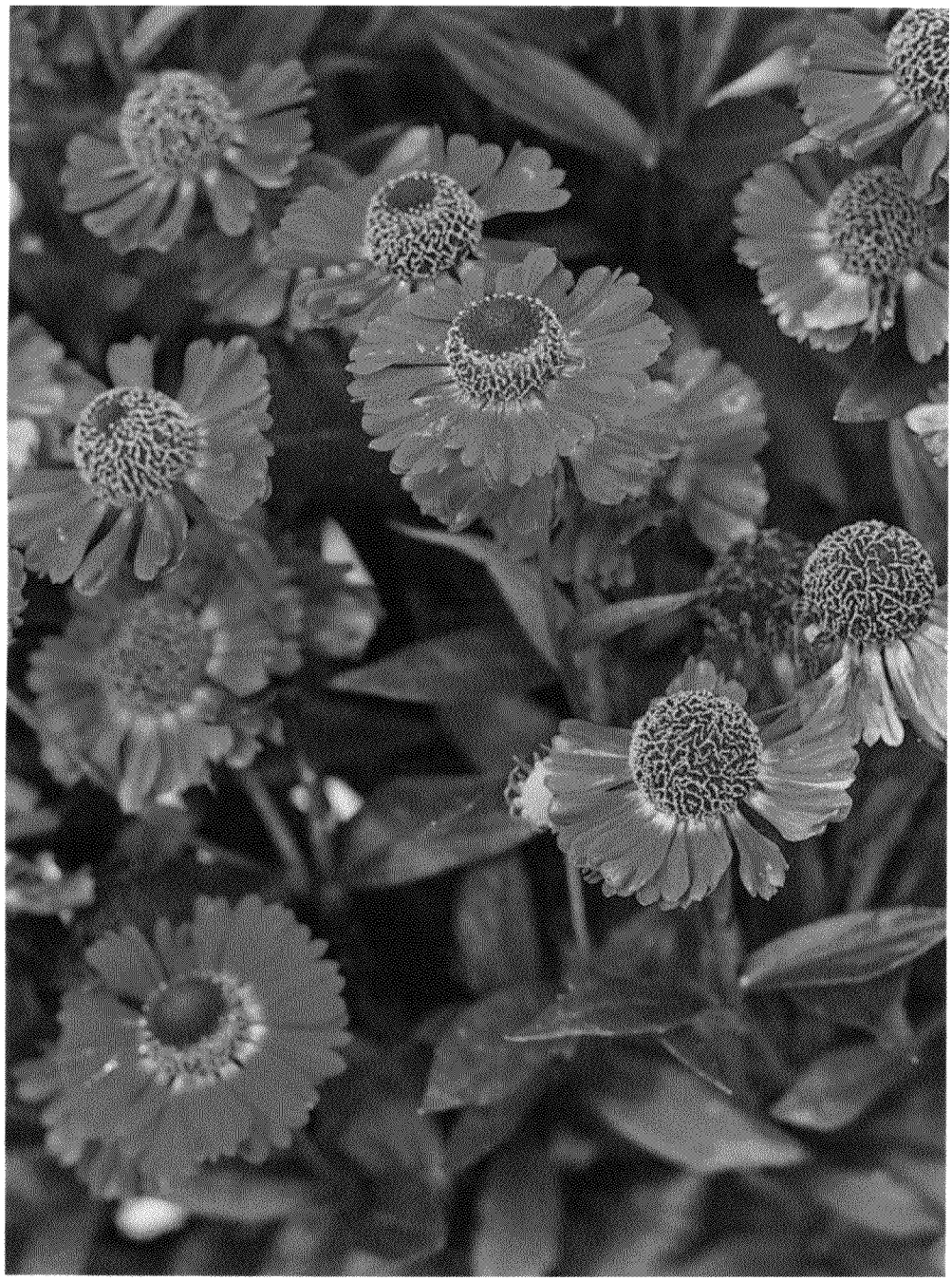

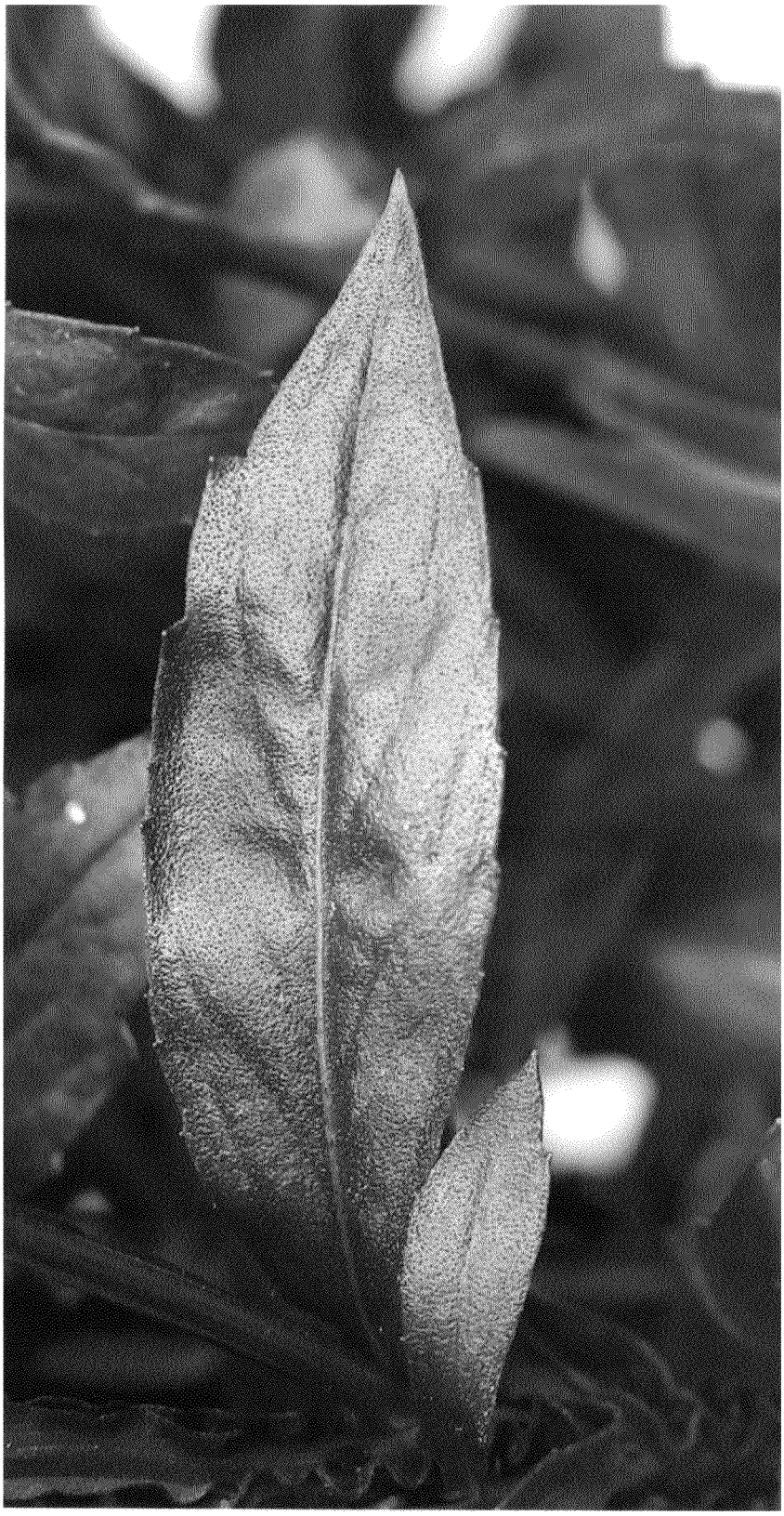

* * * * *